(12) United States Patent
Venczel

(10) Patent No.: US 6,725,721 B2
(45) Date of Patent: *Apr. 27, 2004

(54) ULTRASONIC MULTI-ELEMENT TRANSDUCERS AND METHODS FOR TESTING

(75) Inventor: John Venczel, South Salem, NY (US)

(73) Assignee: Magnetic Analysis Corporation, Mount Vernon, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/101,983

(22) Filed: Mar. 18, 2002

(65) Prior Publication Data

US 2003/0177833 A1 Sep. 25, 2003

Related U.S. Application Data

(60) Provisional application No. 60/338,716, filed on Oct. 22, 2001.

(51) Int. Cl.$^7$ .................................................. G01N 29/04
(52) U.S. Cl. ........................ 73/625; 73/628; 73/622
(58) Field of Search ..................... 73/618, 620, 621, 73/622, 623, 625, 627, 628, 632, 637, 638, 624; 367/103, 105; 29/25, 35

(56) References Cited

U.S. PATENT DOCUMENTS

| | | | | |
|---|---|---|---|---|
| 3,693,415 A | * | 9/1972 | Whittington | 73/67.8 |
| 4,070,905 A | * | 1/1978 | Kossoff | 73/614 |
| 4,254,661 A | * | 3/1981 | Kossoff et al. | 73/625 |
| 4,478,083 A | * | 10/1984 | Hassler et al. | 73/620 |
| 4,676,106 A | * | 6/1987 | Nagai et al. | 73/625 |
| 4,815,043 A | * | 3/1989 | Shirasaka | 367/7 |
| 4,987,563 A | * | 1/1991 | Gilmour | 367/88 |
| 5,123,415 A | * | 6/1992 | Daigle | 73/625 |
| 5,165,414 A | * | 11/1992 | Larson, III | 73/620 |
| 5,297,553 A | * | 3/1994 | Sliwa, Jr. et al. | 29/25.35 |
| 5,460,046 A | * | 10/1995 | Maltby et al. | 73/623 |
| 5,493,541 A | * | 2/1996 | Snyder | 367/155 |
| 5,932,807 A | * | 8/1999 | Mallart | 73/641 |

* cited by examiner

*Primary Examiner*—Helen Kwok
(74) *Attorney, Agent, or Firm*—Fish & Neave; James A. Leiz; Hassan Albakri

(57) ABSTRACT

Ultrasonic multi-element transducers and methods for achieving higher throughput rates in non-destructive testing are provided. By driving the transducer elements sequentially and/or in different combinations, and multiplexing the signals received from each transducer element, the inspection speed at high test sensitivity levels is significantly increased while the number of channels is not increased and cross-talk between the different transducer elements is avoided. At least one such transducer may be mounted on a rotary tester for testing manufactured objects such as tubes and bars.

18 Claims, 11 Drawing Sheets

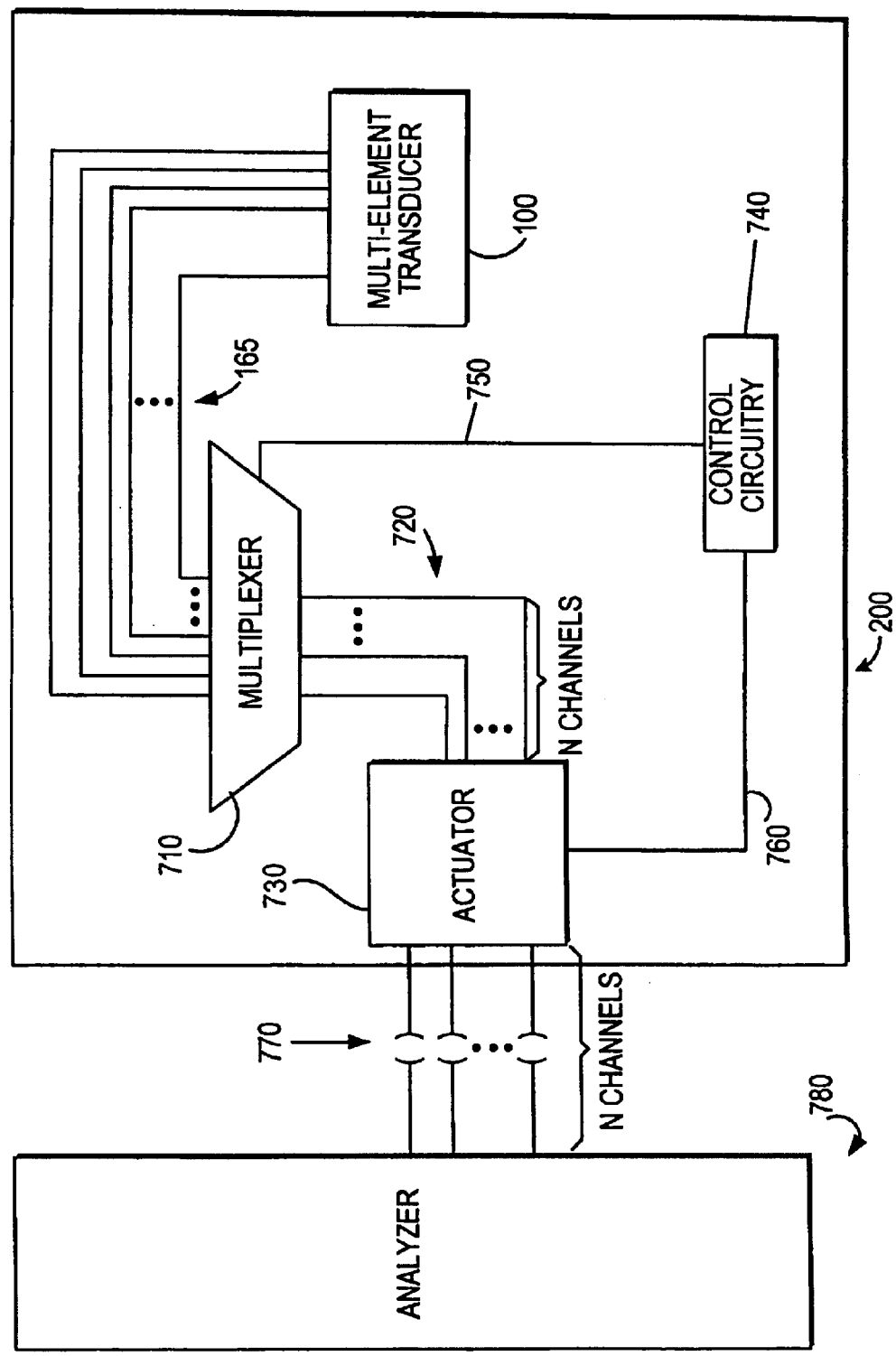

ULTRASONIC MULTI-ELEMENT TRANSDUCERS AND METHODS FOR TESTING

This application claims the benefit of U.S. provisional application No. 60/338,716, filed Oct. 22, 2001, which is hereby incorporated by reference herein in its entirety.

BACKGROUND OF THE INVENTION

The present application relates to an invention for inspecting tubes, bars, pipes, and other objects using ultrasonic transducers. More particularly, the invention is concerned with increasing inspection speed while providing high sensitivity and accuracy for non-destructive testing of such objects.

Ultrasonic inspection is commonly used to detect both surface flaws such as cracks and internal flaws such as voids or inclusions of foreign material. It is also used to measure wall thickness in tubes and pipes as well as bar diameter. In what is known as the pulse-echo method, the same transducer serves both as a transmitter and a receiver of ultrasonic beams or waves used to detect such flaws and take such measurements.

In such a method, in response to an electrical pulse, the transducer produces a pressure wave referred to as an ultrasonic pulse. The pressure wave travels through a coupling medium between the transducer and the tested object. In longitudinal wave inspection, once the ultrasonic pulse reaches an interface between the coupling medium and the tested object, a portion of the pulse enters the object whereas another portion is reflected back to the transducer (i.e., a partial reflection and transmission occur). The initially reflected pulse is known as a frontwall echo. The portion of the pulse that enters the object continues until the back wall, where another partial reflection and transmission occurs. This partial reflection is known as the backwall echo. If there is an internal flaw in the tested object for instance, a portion of the ultrasonic pulse is also reflected back to the transducer at the flaw. The flaw can be located knowing the elapsed time between the different reflections. For automatic flaw testing, a gate is placed between the frontwall and backwall echoes. Any pulse within the gate area is peak detected, producing an analog output that can be recorded and that represents a flaw in the tested object. In addition, thickness measurements are made possible knowing the time difference between the backwall and frontwall echo pulses as well as the velocity of the ultrasonic wave as it travels through the medium of the tested object.

The most widely used pulse-echo process for non-destructive testing of objects such as tubes and bars is performed by using ultrasonic rotary testers. Ultrasonic transducers are mounted on a rotary testing unit of such testers, while the tube or bar to be tested is moved freely through the tester. Rotating the transducers in the tester around the tube as opposed to rotating the tube as it is moved through the tester eliminates the need for heavy machinery and high power in the case of testing large and long tubes and bars. The space between the object and transducers is generally filled with water in order to provide coupling for the ultrasonic beam. The electrical signals from the ultrasonic inspection instrument are connected to the rotating transducers by rotary capacitors. In order to detect various kinds of surface and internal flaws and to provide thickness measures, several transducers are generally mounted on the tester, each being oriented to perform a specific function.

For instance, in a longitudinal wave inspection arrangement, a transducer is typically oriented so that the ultrasonic beam is perpendicular to the surface of the tested object. In such a case, the angle of incidence is 90 degrees. Longitudinal waves are suitable for detecting inner flaws and taking thickness or diameter measurements. When the angle of incidence is not 90 degrees, a refracted shear wave occurs within the tested object. Shear waves are used to detect both surface and internal flaws. Transducers can be oriented to detect both longitudinal and transverse flaws.

To improve the detectability of irregularly shaped flaws, shear waves are generated in both clockwise and counter-clockwise directions. FIG. 1 illustrates a setup for performing such a test with two offset transducers 10. The incident beams 20 of transducers 10 are maintained within the same plane of a cross section that is perpendicular to longitudinal axis 50 of tube 30. Under this setup, beams 22 and 44 travel clockwise and counter-clockwise, bouncing between the outer and inner surfaces of tube 30 until a flaw is detected and beam 20 is partially reflected back to transducer 10. As shown in FIG. 1, the beam traveling clockwise, beam 22, is reflected back from an inner diameter crack 60, while the beam traveling counter-clockwise, beam 44, is reflected back from an outer diameter crack 70.

In another example, the much less common transverse cracks can be detected by angling transducer 10 in a plane containing the longitudinal axis 50 of tube 30, without offsetting transducer 10 from its position when it emits longitudinal beam 20. In such a case the beam would travel along the length of the tube and partially reflect back from transverse cracks.

An entire tube can be scanned if a set of transducers is rotated around the center of the tube while the tube is freely moved along its longitudinal axis. To allow for thickness measurement and to ensure full flaw detection, several transducers are mounted in the rotary tester. Transducers can be oriented generally for longitudinal wave testing and for clockwise, counterclockwise, forward-, and reverse-looking shear wave testing. In this manner, five channels are required so that each transducer can be individually driven.

The linear movement of the tube combined with the rotation of the transducers around the tube results in a helical test path around the circumference of the tube. In order to achieve 100 percent inspection, the helical traces must slightly overlap. The foregoing limits the inspection speed or test throughput rate. If the tube is moved faster, the pitch of the helix increases and the helical traces may cease to overlap. In such a case, gaps may form between separate adjacent helical traces. As a result there would be volumes left untested in the tube. On the other hand, the tester's rotational speed is mechanically limited. In addition, the rate at which a transducer emits an ultrasonic beam, namely, the pulse repetition frequency or rate, should not drop beyond a certain level given the rotational speed of a rotary tester. Moreover, the beam size of the transducer is limited by the required sensitivity of the test itself. The larger the beam, the less sensitive the beam will be to small defects and, as a result, some small defects may not be detected.

However, there has been increasing demand for higher throughput rates and higher testing sensitivities in non-destructive testing of tubes, bars, pipes, etc. With higher throughput rates being especially desirable for online testing (i.e., post manufacturing testing), inspection sensitivity and accuracy cannot be compromised.

It is possible to increase a tester's throughput rate by increasing the number of transducers mounted at different positions on the rotor. Several problems, however, are associated with increasing the number of transducers used.

The number of channels used for analyzing the signals emitted and received from transducers, as well as the number of coupling capacitors required would increase accordingly, which would in turn complicate the required rotary connections. In addition, the mounting space on the rotor may be limited and transducer cross-talk can become a greater problem.

In view of the foregoing, it would be desirable to provide an ultrasonic transducer arrangement for achieving higher throughput rates and higher testing sensitivities during ultrasonic testing.

It would be further desirable to provide an ultrasonic transducer arrangement that would maximize test sensitivity given mechanical limitations in rotary testers and pulse repetition requirements.

It would be further desirable to provide an ultrasonic transducer arrangement that makes efficient use of space on rotary testers without increasing the number of channels and capacitors needed.

SUMMARY OF THE INVENTION

It is therefore an object of the present invention to provide ultrasonic transducer systems and methods for achieving higher throughput rates and higher testing sensitivities during ultrasonic testing.

It is another object of the present invention to provide ultrasonic transducer systems and methods that maximize test sensitivity given mechanical limitations in rotary testers and pulse repetition requirements.

It is another object of the present invention to provide ultrasonic transducer systems and methods that make efficient use of space on rotary testers without increasing the number of channels and capacitors needed.

These and other objects of the present invention are accomplished by providing a multi-element transducer containing multiple transducer elements that may be driven individually or in groups. Each transducer element or adjacent groups of transducer elements are capable of producing an ultrasonic beam with a desirable beam length that meets inspection sensitivity requirements. At least one such multi-element transducer may be mounted on a rotary tester that may be programmably controlled for testing manufactured objects such as tubes and bars. Given the mechanical and pulse repetition limitations in rotary testers, the provided systems and methods for non-destructive testing achieve higher throughput rates. The multi-element transducer may be positioned for performing longitudinal wave inspection or shear wave inspection for detecting different kinds of flaws as well as for measuring tube thickness and bar diameter.

In one suitable approach, individual transducer elements or adjacent transducer elements may be driven during different firing periods. In another suitable approach, two or more individual transducer elements, or groups of adjacent transducer elements, each separated by at least one transducer element, may be driven during different firing periods. The signals received from the individual or groups of transducer elements may be multiplexed to decrease the number of channels required for analyzing. A channel may be used for analyzing the signals received from an individual transducer element or group of transducer elements. Once a desired amount of time has passed, signals from another individual transducer element or group of transducer elements may be switched to the channel for analyzing. This increases the inspection speed without increasing the number of channels used.

Tubes have properties that make them especially useful for the purpose of illustrating the present invention and, therefore, will be used in the following discussion with the fundamental tenet that the principles discussed may be applied to other types of manufactured objects without departing from the concepts in this invention.

BRIEF DESCRIPTION OF THE DRAWINGS

Further features of the invention, its nature and various advantages will be more apparent from the following detailed description of the preferred embodiments, taken in conjunction with the accompanying drawings, in which like reference characters refer to like parts throughout, and in which:

FIG. 13 is a general schematic of a system in which a multi-element transducer may be used for non-destructive testing, in accordance with certain embodiments of the present invention.

DETAILED DESCRIPTION OF THE PRESENT INVENTION

In order to achieve high throughput rates for ultrasonic testing, a transducer element may be divided into a multiple number of transducer elements that may be individually or collectively driven. Each transducer element may be excited to produce an ultrasonic pulse from an electrical pulse. Likewise, each transducer element may produce an electrical pulse from receiving an ultrasonic pulse. Each transducer element, or combination of adjacent transducer elements, may be capable of producing an ultrasonic beam with a desirable beam size that meets inspection sensitivity requirements. This arrangement increases the number of transducer elements for the given task. The advantages of the present invention will be apparent upon consideration of the following.

Figure 2:
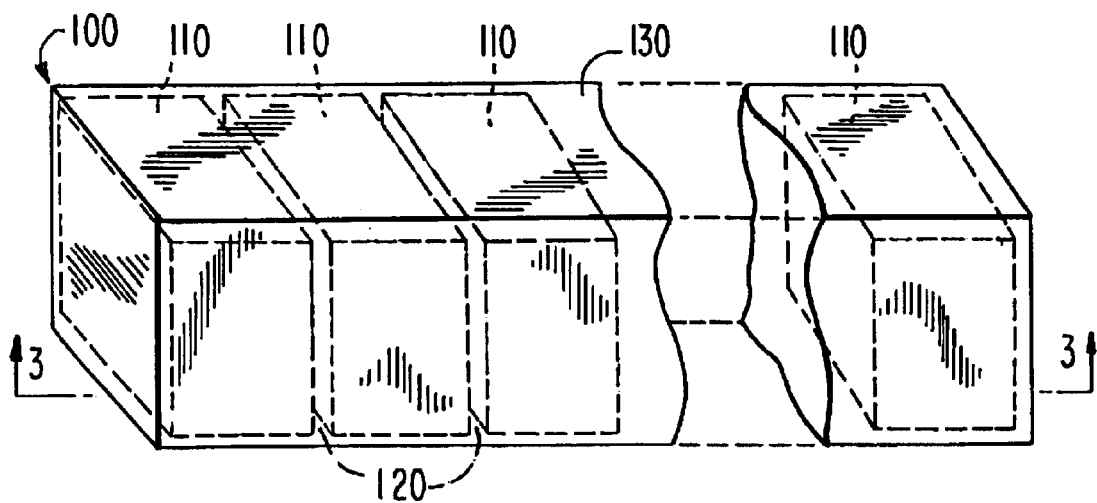
FIG. 2 is a perspective view of an illustrative general multi-element transducer, in accordance with certain embodiments of the present invention.

FIG. 2 is a perspective view of an illustrative general multi-element transducer 100. Multi-element transducer 100 may include multiple transducer elements 110. As illustrated, transducer elements 110 are linearly arranged. Transducer elements 110 may, however, be arranged in any suitable arrangement. Transducer elements 110 are separated by gaps 120. Gaps 120 function to isolate transducer elements 110 from each other so that they can be separately driven. In another suitable approach, gaps 120 may contain a material to isolate transducer elements 110. Housing 130 may contain transducer elements 110. Housing 130 may be any suitable housing such as an IF or flange type housing.

Figure 3:
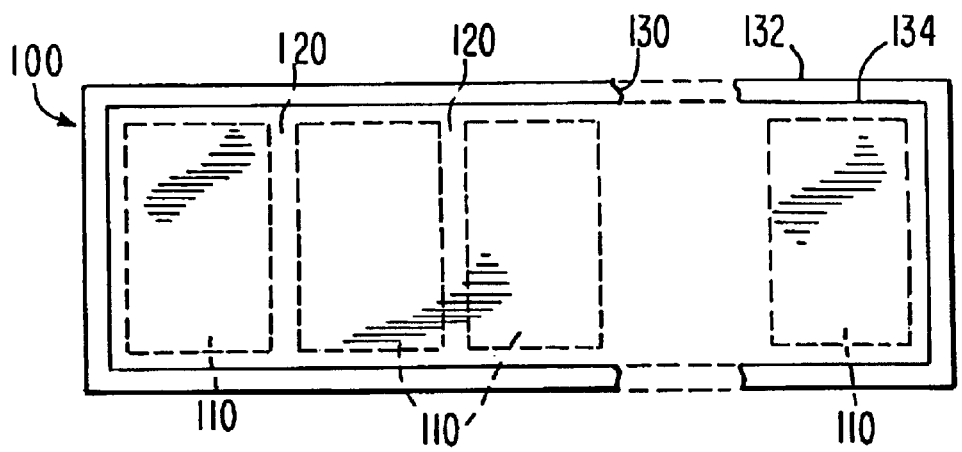
FIG. 3 is a sectional view of the multi-element transducer of FIG. 2, taken generally along the line 3—3, in accordance with certain embodiments of the present invention.

FIG. 3 is a sectional view of multi-element transducer 100 taken generally along the line 3—3 of FIG. 2. FIG. 3 shows the surface of transducer elements 110 from which ultrasonic pulses may be emitted and received. Housing 130 has inner surface 134 and outer surface 132. The bottom part of housing 130, covering the surface of transducer elements 110, may be transparent to ultrasonic waves in order to allow ultrasonic pulses to travel back and forth from and to transducer elements 110. In another suitable arrangement, the bottom part of housing 130 may not cover the surface of transducer elements 110. While multi-element transducer 100 is illustrated as a linear array, multi-element transducer 100 may also contain multiple rows of transducer elements 110.

Figure 4:
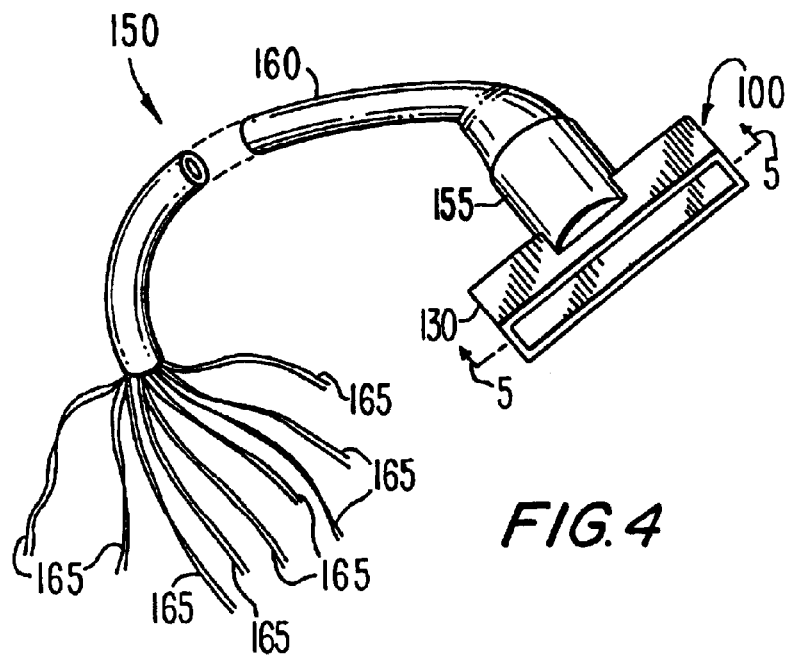
FIG. 4 is a perspective view of an illustrative ultrasonic multi-element transducer, in accordance with one embodiment of the present invention.

In FIG. 4, a preferred embodiment of multi-element transducer 100 is depicted as part of transducer 150. Transducer 150 includes nine transducer elements 110 within multi-element transducer 100. Transducer 150 will be described in detail as a transducer for testing bars and tubes with an outer diameter of approximately 2.5 inches. However, it is understood that the present invention may be used with bars and tubes of any suitable outer diameters. Each of transducer elements 110 preferably has a length 112 of 0.25 inches and a width 114 of 0.375 inches for testing bars and tubes with an outer diameter of approximately 2.5 inches. Gaps 120 between transducer elements 110 may be of negligible length. As a result, the array of transducer elements 110 may be about 2.25 inches long. Transducer elements 110 may be made of any suitable material such as piezoelectric material. Transducer elements 110 are preferably made of thin rods of piezoelectric ceramic elements embedded into a polymer material. The electrical and ultrasonic properties of multi-element transducer 100 may depend on the microstructure and the properties of the materials constituting transducer elements 110.

Each transducer element 110 is preferably connected to a coaxial cable 165 through extension 155. There are preferably nine coaxial cables 165, contained within shielding cable 160, each dedicated to one of transducer elements 110. Signals sent through cables 165 may drive transducer elements 110 individually, collectively, or in different grouping arrangements, which will be described in more detail in the following. When all of transducer elements 110 are connected and driven in parallel, multi-element transducer 100 acts like a single transducer emitting a relatively long ultrasonic beam, because gaps 120 are of negligible length. Multi-element transducer 100 is preferably cylindrically focused with a focal length of 2.5 inches for testing bars and tubes with an outer diameter of approximately 2.5 inches.

Figure 5:
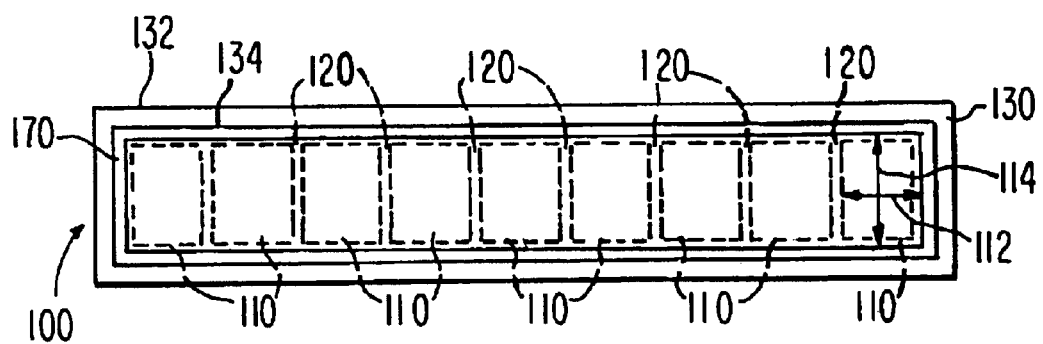
FIG. 5 is a sectional view of the multi-element transducer of FIG. 4, taken generally along the line 5—5, in accordance with one embodiment of the present invention.

FIG. 5 is a sectional view of the multi-element transducer 100 of FIG. 4 taken generally along the line 5—5 of FIG. 4. FIG. 5 shows the surface of transducer elements 110 from which ultrasonic pulses may be emitted and received. Housing 130 as illustrated in FIGS. 4 and 5 is a standard IF case and has inner surface 134 and outer surface 132. Transducer elements 110 may be contained within rectangular enclosure 170 that is attached to inner surface 134 of housing 130.

The previous discussion relating to FIGS. 4 and 5 describes one particular embodiment of multi-element transducer 100. However, the dimensions and properties of multi-element transducer 100 are not limited to the ones mentioned above and may be varied based on the dimensions and properties of the object to be tested.

Figure 6:
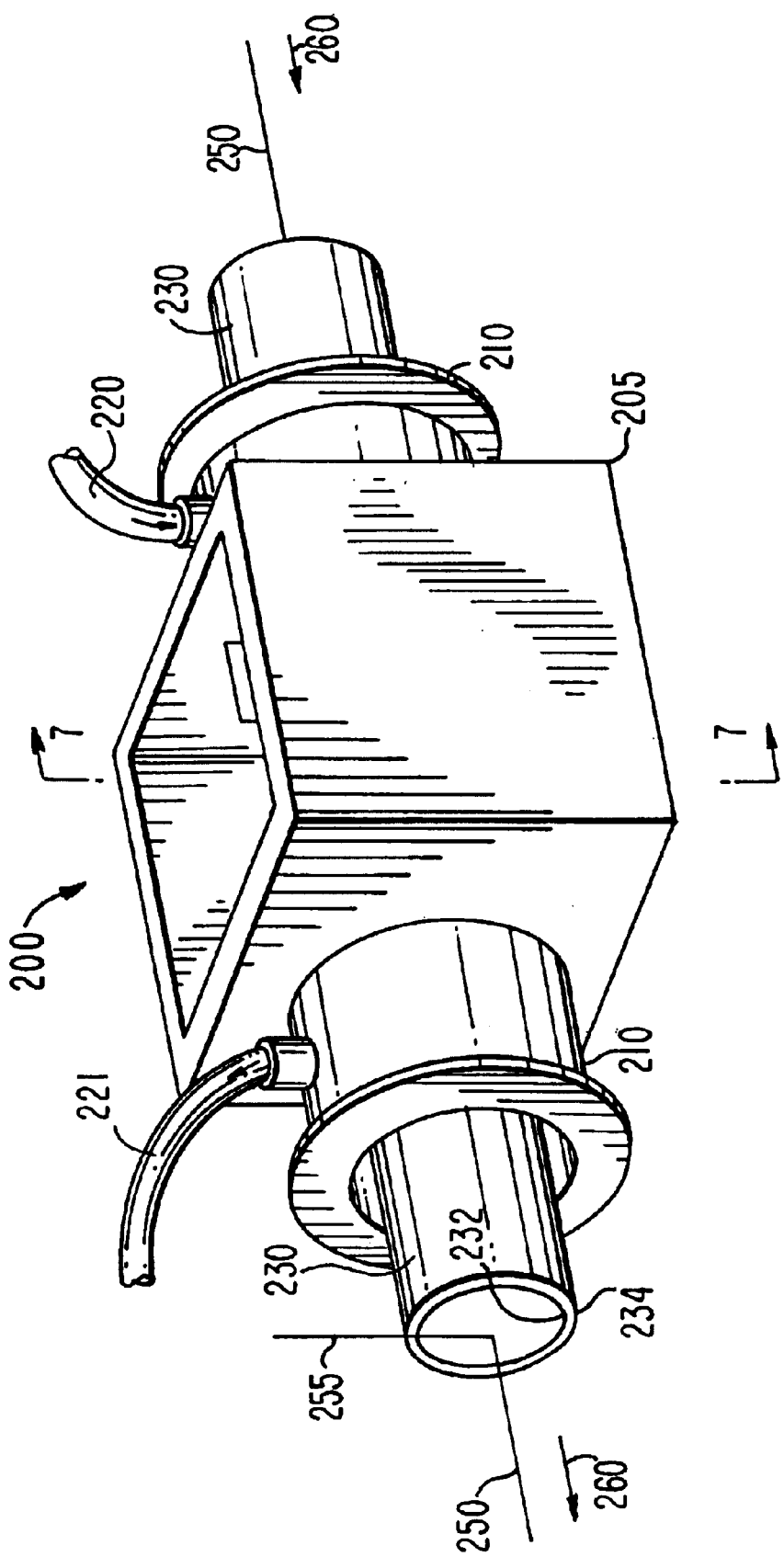
FIG. 6 is a perspective view of an illustrative tube being tested by an illustrative rotary tester, in accordance with one embodiment of the present invention.

FIG. 6 illustrates a tube 230 being tested by rotary tester 200. Tube 230 has longitudinal axis 250. The main body of tester 200 may be enclosed within a cubical frame 205, from which two outer shafts 210 extend. Tube 230 enters tester 200 from one of outer shafts 210 such that the center of tube 230 (i.e., longitudinal axis 250) passes through the centers of shafts 210 and tester 200. Tube 230 may also be allowed to move freely in direction 260 along the tube's longitudinal axis 250 without directly coming in contact with any part of tester 200. Tube 230 is shown to have inner surface 232 and outer surface 234. Tester 200 may include a testing unit (not shown in FIG. 6, but shown in FIG. 7), which is enclosed within cubical frame 205. Hoses 220 and 221 can be used to deliver and cycle coupling medium to and through tester 200. The coupling medium (not shown in FIG. 6, but shown in FIG. 7) may be any suitable medium in which ultrasonic waves may propagate freely. Water may be chosen as coupling medium mainly because it is inexpensive. As tube 230 is being tested, the coupling medium may be delivered through hose 220 at one of outer shafts 210, while the coupling medium may exit through hose 221 at the other outer shaft 210. As tube 230 is moved through tester 200, the coupling medium may be pumped and cycled through the testing unit in tester 200. Shafts 210 may include seals that may keep the water contained within the testing unit.

Figure 7:
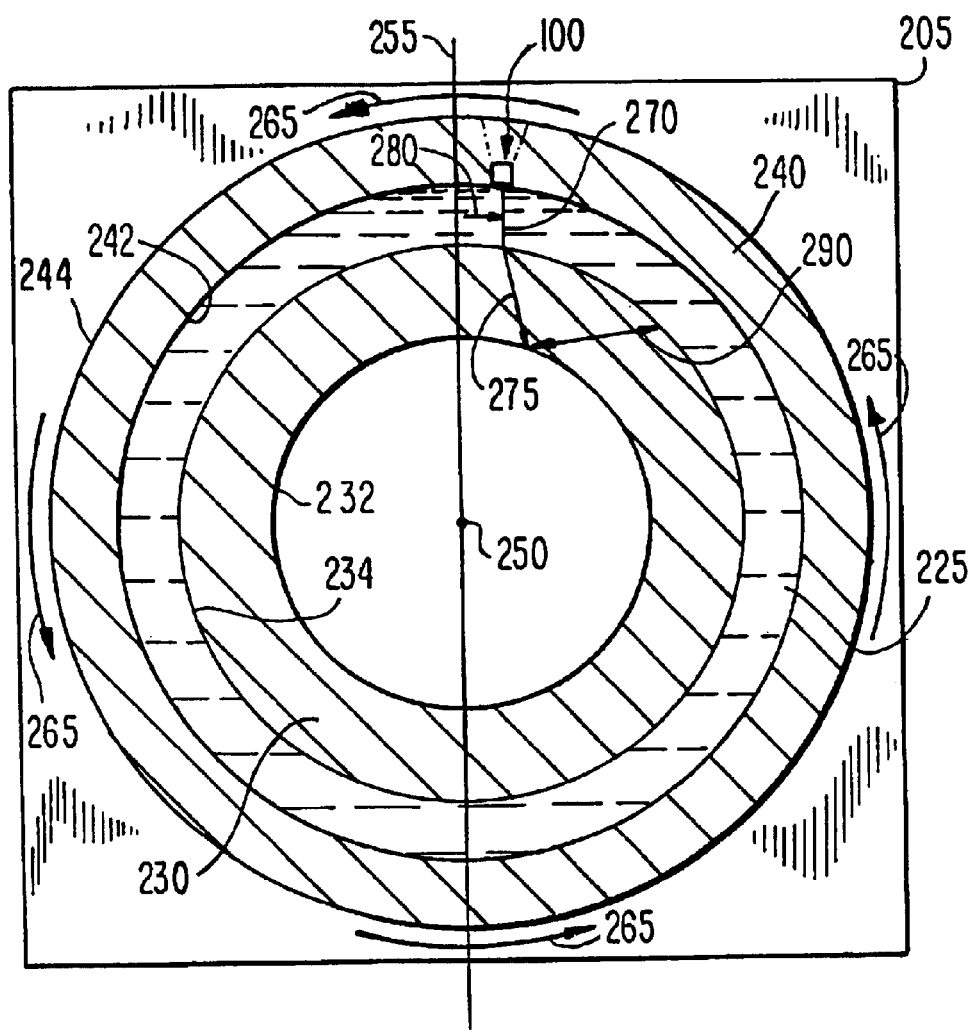
FIG. 7 is a cross-sectional view of the rotary testing unit and tube of FIG. 6, taken generally along the line 7—7, in accordance with one embodiment of the present invention.

As previously mentioned, tube 230 may be rotated about axis 250 as it is being tested. However, as shown in FIG. 7, which is a cross-sectional view of rotary tester 200 and tube 230 taken generally along line 7—7 of FIG. 6, testing unit 240, which is enclosed within cubical frame 205, may be rotated about axis 250 in, for example, counter-clockwise direction 265. Coupling medium 225 remains in contact with both the outer surface 234 of tube 230 and the inner wall 242 of testing unit 240, therefore filling the space between tube 230 and testing unit 240 during testing.

In addition to longitudinal axis 250, which intersects the centers of both tube 230 and testing unit 240, there is radial axis 255, which is perpendicular to and intersects longitudinal axis 250, and lies within the plane of FIG. 7. As testing unit 240 is rotated about longitudinal axis 250, radial axis 255 rotates about longitudinal axis 250 as well. Multi-element transducer 100 may be mounted within testing unit 240 and oriented depending on what is being tested for such as inclusions, surface/internal cracks, thickness consistency, etc. For example, to test for inner flaws and to measure tube thickness, a longitudinal wave inspection arrangement may be used. In such an arrangement, which is not depicted in FIGS. 7 and 8, the multi-element transducer may be oriented so that the emitted ultrasonic beam is perpendicular to tested tube 230's surface. In other words, the ultrasonic beam remains in line with the radial axis during longitudinal wave inspection, as the multi-element transducer is rotated around the tube about longitudinal axis 250.

Figure 8:
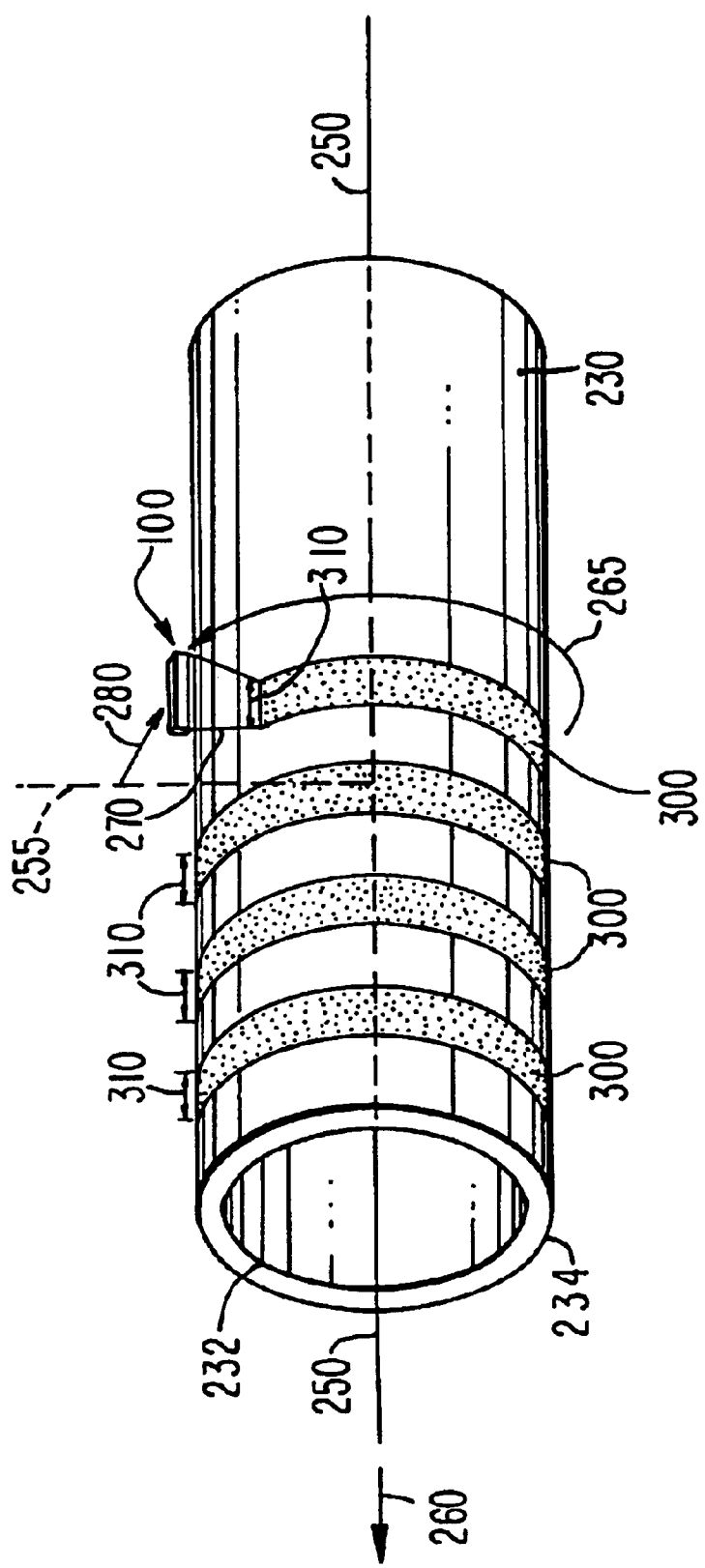
FIG. 8 is a perspective view of an illustrative test pattern along the tube being tested, in accordance with one embodiment of the present invention.

A shear wave inspection arrangement is illustrated in FIGS. 7 and 8, in accordance with the principles of the present invention. In such an arrangement, multi-element transducer 100 may be mounted within testing unit 240 and oriented so that the emitted ultrasonic beam 270 is not perpendicular to tube 230's outer surface 234. The previously discussed transducer elements of multi-element transducer 100 may be aligned in a linear array such that the linear array of multi-element transducer 100 is parallel to longitudinal axis 250. Because the angle of incidence is not 90 degrees, a portion of the incident beam 270 may be refracted at the interface between coupling medium 225 and outer surface 234 of tube 230. As illustrated, refracted beam 275 may travel clockwise through tube 230, partly reflecting between inner surface 232 and outer surface 234, until beam 270 reaches a flaw 290. Beam 270 may then be reflected back from flaw 290 to multi-element transducer 100.

In order to produce shear waves such as ultrasonic beam 275, multi-element transducer 100 may be offset in direction 280 from its position if it were to emit a beam perpendicular to tube 230's outer surface 234, as shown in FIG. 7. The offset in direction 280 may be in either direction away from radial axis 255, provided the offset is contained within the same plane perpendicular to longitudinal axis 250 and containing radial axis 255, and provided multi-element transducer 100 is parallel to longitudinal axis 250. These conditions hold as testing unit 240 and multi-element transducer 100 are rotated about longitudinal axis 250. The amount of the offset in direction 280 may depend on various factors such as the material being tested (the velocity of sound in the material of tube 230), the diameter of tube 230, etc. To produce a counter-clockwise refracted shear beam, multi-element transducer 100 may simply be offset from axis 255, in the direction opposite to direction 280.

Figure 1:
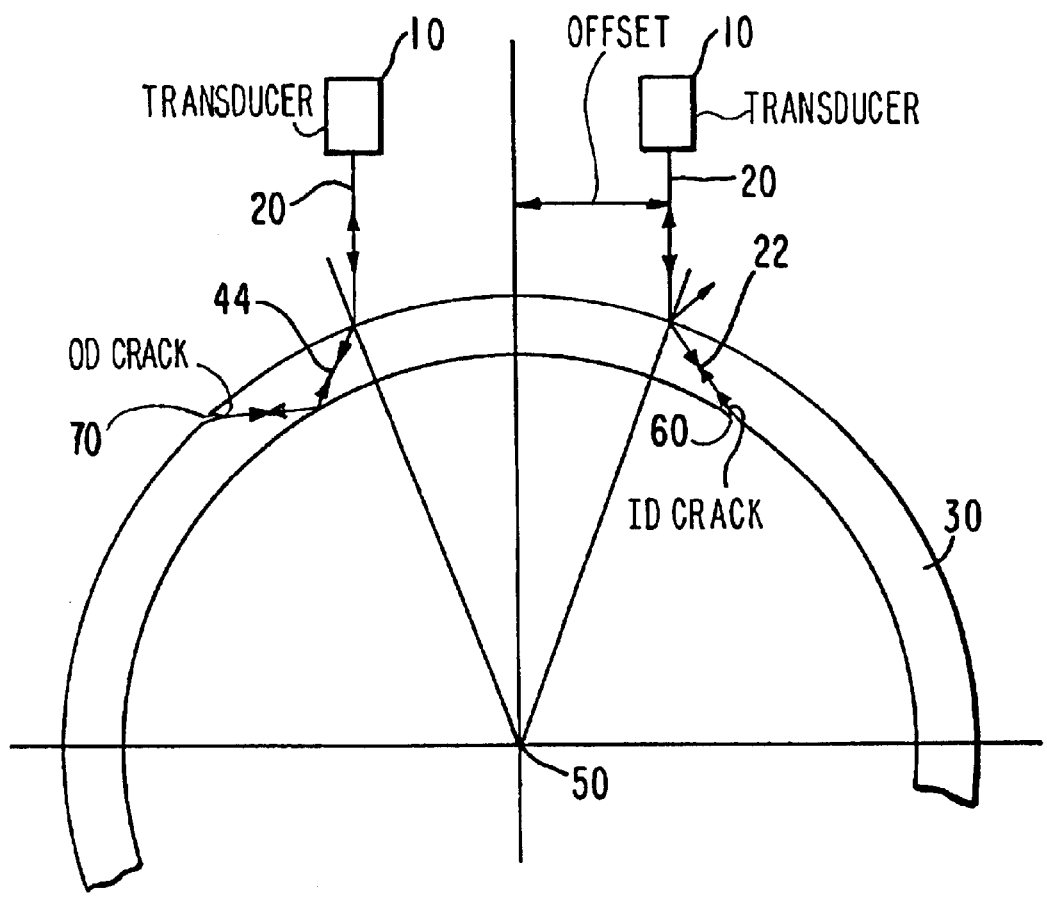
FIG. 1 is a cross-sectional view of a tube with two transducers in a conventional arrangement for performing shear wave testing.

FIG. 8 is a perspective view of an illustrative test pattern along tube 230. A single multi-element transducer 100 is shown to be parallel to longitudinal axis 250, offset from radial axis 255 in direction 280, in order to perform shear wave testing. FIGS. 7 and 8 illustrate only one multi-element transducer 100 that is mounted in testing unit 240 for performing clock-wise shear wave testing. In operation, typically two transducers may be used as shown in FIG. 1, one producing a clockwise refracted shear beam, and the other producing a counter-clockwise refracted shear beam. Referring to FIGS. 7 and 8, an additional multi-element transducer (not shown) may therefore be mounted on testing unit 240 and offset in a direction opposite to direction 280, so that a beam may be reflected counter-clockwise through tube 230 as shown in FIG. 1.

As shown in FIG. 8, tube 230 may be moved in direction 260 while multi-element transducer 100 rotates about longitudinal axis 250 in direction 265, during testing. This combination of motions results in helical test traces 300 around the circumference of tube 230. Test traces 300, as illustrated, have gaps between each subsequent test trace. This is for illustration purposes only.

Helical traces 300 must slightly overlap to ensure reliable flaw detection and achieve 100 percent inspection. If tube 230 is moved faster in direction 260, given the same incident beam length 310 on surface 234 and the same rotational speed in direction 265, there may be untested volumes on tube 230. The following equation relates the preceding elements:

$$V_{max} = \beta_1 \cdot \omega$$

where $V_{max}$ denotes the maximum inspection velocity (i.e., the maximum speed at which the testing can be conducted), which also establishes the test throughput rate. $\beta_1$ denotes the incident beam length whereas $\omega$ denotes the rotational speed of the tester. Because ultrasonic beam 270 is cylindrically focused and because the intensity around the edges of multi-element transducer 100 drops, the incident beam length 310 is generally less than the total length of multi-element transducer 100.

Because the rotational speed is limited by pulse repetition frequency requirements in addition to mechanical limitations of the tester, the incident beam length, in the present invention, is increased by providing a multi-element transducer 100. This in turn increases the inspection velocity or test throughput rate. However, the longer the beam, the less sensitive it is to small flaws, the less accurate the test. Because multi-element transducer 100 includes an array of multiple smaller transducer elements, capable of being driven individually, collectively, or in any desired combination, a desired beam length may be achieved by driving the appropriate transducer elements in certain combinations. The following discussion provides some examples of different firing arrangements in connection with, but not limited to, longitudinal wave testing. Eliminating the offset in direction 280 (i.e., making the offset distance equal to zero) would result in a longitudinal wave testing arrangement.

Figure 9:
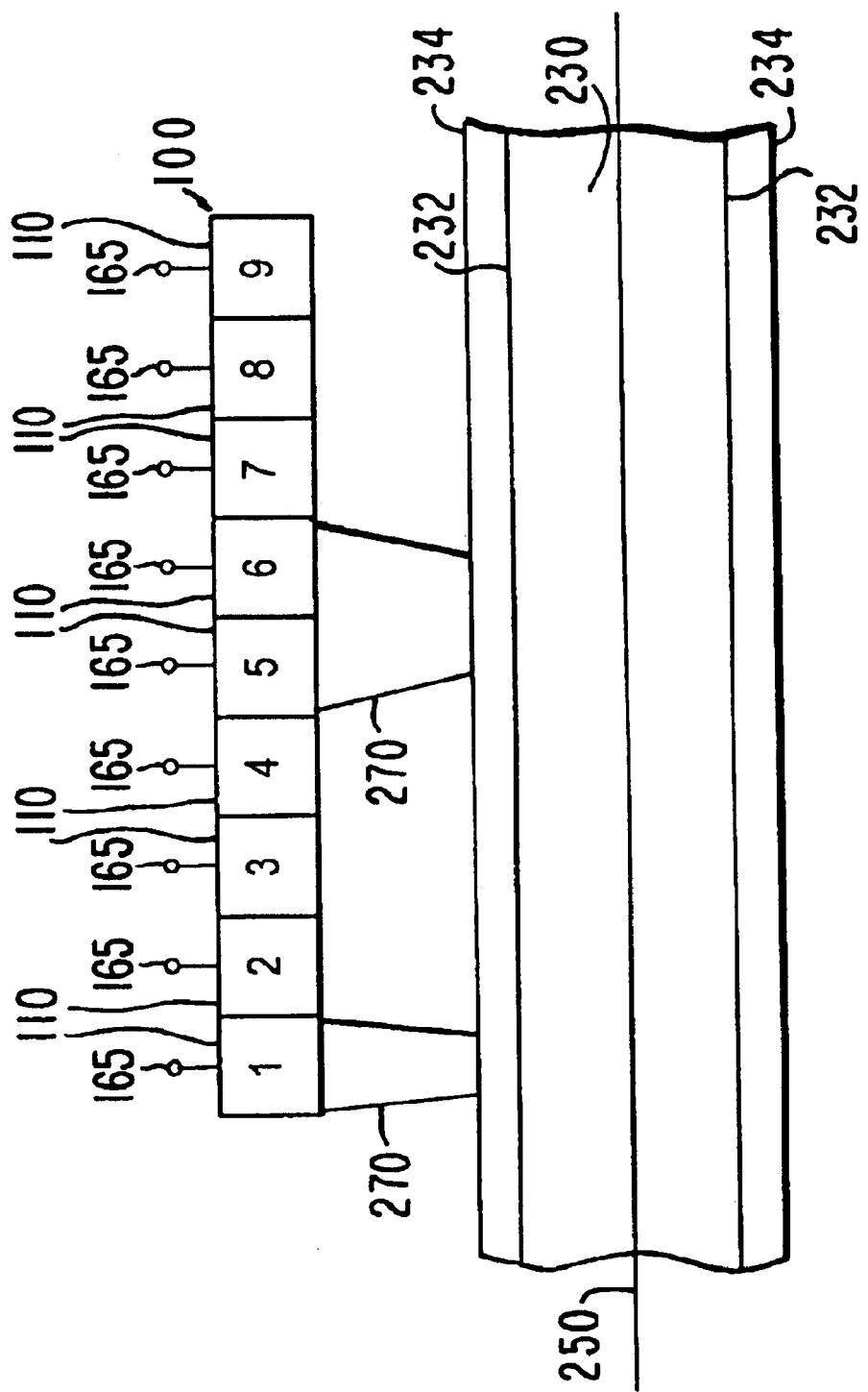
FIG. 9 is a side view of an illustrative multi-element transducer as it emits ultrasonic beams onto a tube, in accordance with certain embodiments of the present invention.

Multi-element transducer 100, as shown in FIG. 9, is composed of nine transducer elements 110 numbered 1 through 9. Multi-element transducer 100 may be positioned so that it is parallel to tube 230's longitudinal axis 250. Each transducer element 110 may be driven and monitored through its associated cable 165. In order for testing to be maintained at relatively high speeds, transducer elements 110 may be stimulated to emit beams individually or in groups. For example, it is possible for the first transducer element to emit beam 270. It is further possible for the fifth and sixth transducer elements to emit the larger beam 270 on a different section of tube 230. Connecting two adjacent transducer elements in parallel may produce an ultrasonic beam of desired length. Firing more than one group of two transducer elements simultaneously is made possible by dedicating different channels to each group of transducer elements.

However, dedicating a separate channel to every transducer element or group of transducer elements may complicate wiring and processing on the rotary tester, which may also result in cost increases. Therefore, in another aspect of the present invention, each transducer element, or group of transducer elements may be driven sequentially with their respective signals multiplexed into one or more channels. For this to be done without reducing the pulse repetition frequency, signals received from each transducer element or group of transducer elements may be sequentially switched, resulting in the cropping of such signals once a specific time period has elapsed or a desired number of echoes is obtained. The following discussion illustrates how this may be achieved.

Figure 10:
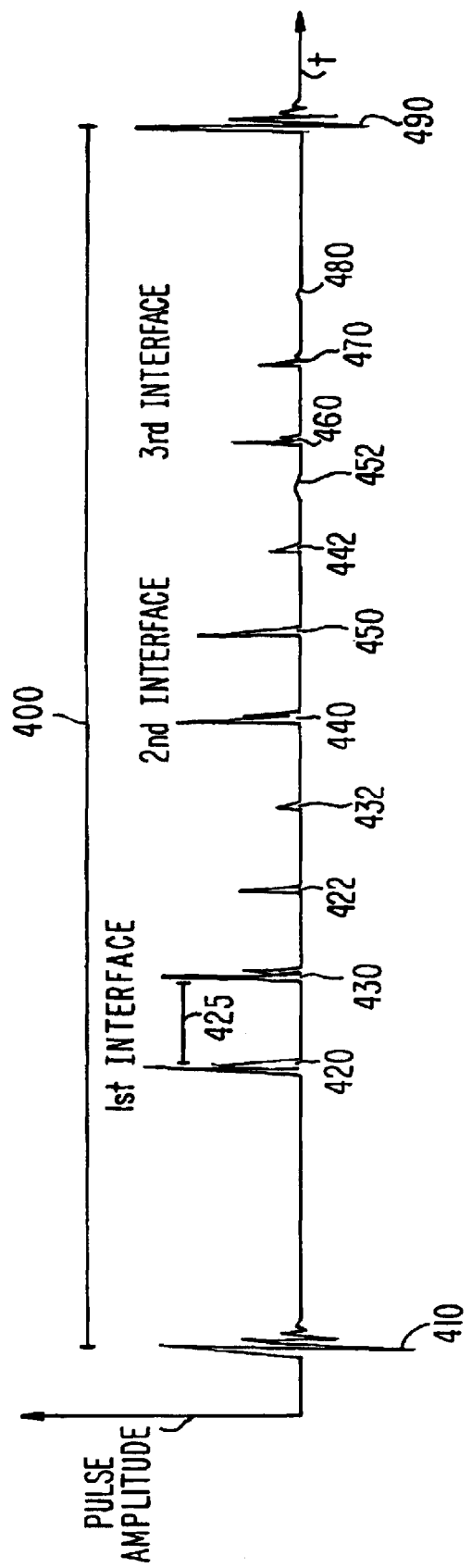
FIG. 10 is a waveform of an illustrative ultrasonic test period.

FIG. 10 illustrates a waveform of an uncropped ultrasonic test period 400 of a longitudinal wave inspection, in which the amplitudes of the pulses sent and received by a transducer are graphed versus time. Test period 400 may start with initial pulse 410 and end with initial pulse 490 from the next test period. Pulse 420 is an ultrasonic echo representing the wave reflected back from the outer surface of the tube being tested at the first interface (i.e., the first reflection of the initial beam from the outer surface of the tested object). Assuming water is used as coupling medium, the time difference between pulses 410 and 420 represents the transit time of the initial pulse in the water path to and from the outer surface of the tube. Pulse 430 is an ultrasonic echo representing the wave reflected back from the inner surface of the tube being tested at the first interface. Pulses 420 and 430 may be referred to as first frontwall echo and first backwall echo respectively. After pulses 420 and 430 are received, several echoes representing the multiple reflections from the inner and outer surfaces of the tube at the first interface may follow. Pulses 422 and 432 represent such echoes which may have smaller amplitudes.

In addition, some of the pulses depicted in FIG. 10 may represent subsequent reflections between the outer surface of the tube and the face of the transducer in subsequent interfaces. For example, pulses 440 and 450 may represent second frontwall and backwall echoes at a second interface (i.e., the second reflection of the initial beam from the outer surface of the tested object) respectively, while pulses 442 and 452 may represent additional reflections from inner and outer surfaces of the tube following the second interface. In addition, there may be other subsequent reflections at subsequent interfaces (i.e., subsequent reflections of the initial beam from the outer surface of the tested object), as well as subsequent inner and outer surface reflections resulting in echoes such as the ones represented by pulses 460, 470 and 480. As can be seen from FIG. 10, as time passes, the pulse amplitudes of the echos generally decrease. This may be largely due to the multiple reflections between the several walls which attenuate the signal amplitude. Test period 400 ends once all multiple echoes are reduced to approximately zero, and a new initial pulse 490 is transmitted.

The ultrasonic test may be performed by monitoring the time interval between first frontwall echo 420 and first backwall echo 430. This time interval may be referred to as flaw gate 425. For example, in the case of an internal flaw, an echo may appear in flaw gate 425. For automatic inspection, any pulses in flaw gate 425 are peak detected and characterized as flaws if they exceed a specified pulse amplitude threshold. In FIG. 10, no flaws are represented.

From the foregoing, it should be clear that after the occurrence of first backwall echo 430, ultrasonic flaw detection may be complete for longitudinal wave testing. However, in typical ultrasonic tests, the next test period cannot be started until all multiple echoes are reduced to approximately zero. For example, an ultrasonic test period that lasts around 500 microseconds produces a pulse repetition frequency of about 2 kHz. This pulse repetition frequency may be significantly increased when a multi-element transducer such as the one described above is used. This can be achieved by driving each transducer element or group of transducer elements individually and switching to drive another transducer element or group of transducer elements after the first backwall echo is received by the first emitting transducer element or group of transducer elements, and so on.

Figure 11:
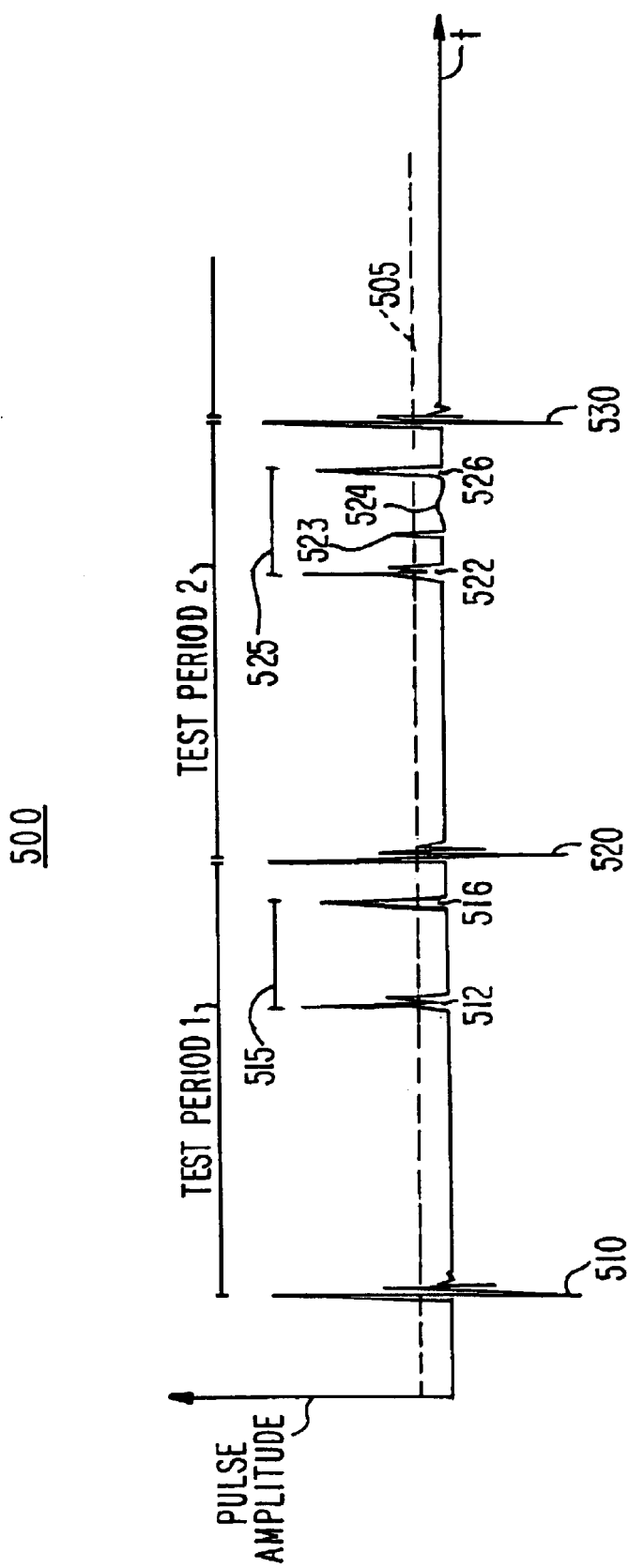
FIG. 11 is a waveform of an illustrative ultrasonic test period, in accordance with certain embodiments of the present invention.

FIG. 11 illustrates a waveform 500 that may be achieved through the use of an ultrasonic multi-element transducer, in which the amplitudes of the pulses sent and received by a multi-element transducer are graphed versus time. A channel may be dedicated to a transducer element or group of transducer elements which may be driven initially. As a result, a first test period may start with initial pulse 510 and end with initial pulse 520 from the next test period. Pulse 512 is the first frontwall echo and pulse 516 is the first backwall echo. Flaw gate 515 is the time interval between first frontwall echo 512 and first backwall echo 516, in the first test period. Assuming water is used as coupling medium, the time difference between pulses 510 and 512 represents the transit time of the initial pulse in the water path to and from the surface of the tube. If at least one echo in flaw gate 515 reaches an amplitude exceeding threshold 505, the echo is considered to represent a flaw. During the illustrative first test period of FIG. 11, no flaws are detected.

After first backwall echo 516, the channel may be switched and dedicated to a different transducer element or group of transducer elements to be subsequently driven. Because the newly driven transducer element or group of transducer elements do not face the same portion of the surface of the tube being tested as the previous transducer element or group of transducer elements may have faced, at least a partially different volume of the tube may be tested upon switching. As a result, a second test period may start with initial pulse 520 and end with initial pulse 530 from the next test period. Pulse 522 is the first frontwall echo and pulse 526 is the first backwall echo. Flaw gate 525 is the time interval between first frontwall echo 522 and first backwall echo 526, in the second test period. The time difference between pulses 520 and 522 represents the transit time of the second initial pulse in the water path to and from the surface of the tube. If at least one echo in flaw gate 525 reaches an amplitude exceeding threshold 505, the echo is considered to represent a flaw. During the second test period, echo 523 exceeds threshold 505 whereas echo 524 does not. As a result, only echo 523 may be characterized as representing a flaw in the tube being tested. Such flaw detection may be automated by presetting a global threshold 505 and using a programmable control, such as a computer or any other suitable device, that may monitor flaw gates 515 and 525. The computer may run a peak detection algorithm and establish flaws based on whether the amplitude of pulses within such flaw gates exceed the predetermined threshold 505.

It should be clear that the discussion above may apply to bars as well. Once a first backwall echo occurs, the channel may be switched and dedicated to a different transducer element or group of transducer elements to be subsequently driven, resulting in a new test period as described above, and so on.

Furthermore, the longitudinal wave testing arrangement described above may be used for acquiring thickness and diameter measurements. The distances traveled in the tested object and the time segments of the pulses received are proportional in the same material, because the sound velocity is constant within a material. By calibrating a particular specimen with a given sound velocity, the elapsed time between first frontwall pulse 512 and first backwall echo pulse 516 in FIG. 11 may be translated to a measure of thickness in the case of a tube, and diameter in case of a bar. This process may also be automated for each test using a programmable control that may record the length of flaw gates 515 and 525 and calculate the corresponding thickness by multiplying the elapsed time by the ultrasonic wave velocity in the material of the object being tested.

It should be noted that switching test periods may be implemented in fixed time intervals. That is, instead of waiting for a first backwall echo to be received before emitting a new initial pulse, the tester may be programmed so that a predetermined amount of time elapses before emitting the new initial pulse. This predetermined amount of time may be greater than the amount of time needed to receive a first backwall echo, and may be calculated or determined based on the properties of each tested object, such as dimensions and material. Furthermore, when shear wave testing is used, such switching according to a fixed elapsed time interval is preferably used in order to allow enough time for a refracted initial pulse to travel clockwise or counterclockwise through a desired portion of the object.

Referring back to FIG. 9, the intensity of ultrasonic beams 270 may not be uniform along the length of a transducer element 110. While the beam intensity may be fairly uniform for the center of each transducer element 110, it may drop to, for example, about 50 percent of its maximum value along the transducer element's edges. Moreover, an ultrasonic beam 270 is typically cylindrically focused so that its focal point lies along longitudinal axis 250, when multi-element transducer 100 is positioned as shown in FIG. 9. This may result in untested gaps on the surface of tube 230 because the area of incident beam 270, as it reaches the surface of tube 230, is smaller than when it is emitted. However, firing multiple transducer elements simultaneously and sequentially can solve such problems, while at the same time satisfying overlap testing requirements. As a result, there is a tradeoff between test sensitivity and coverage when considering the number of transducer elements to be stimulated simultaneously. In accordance with a preferred embodiment of this invention, a desired beam length and overlap coverage may be obtained by simultaneously firing two transducer elements 110 and repeating such firing for other groups of transducer elements 110 as will be described below.

Figure 12:
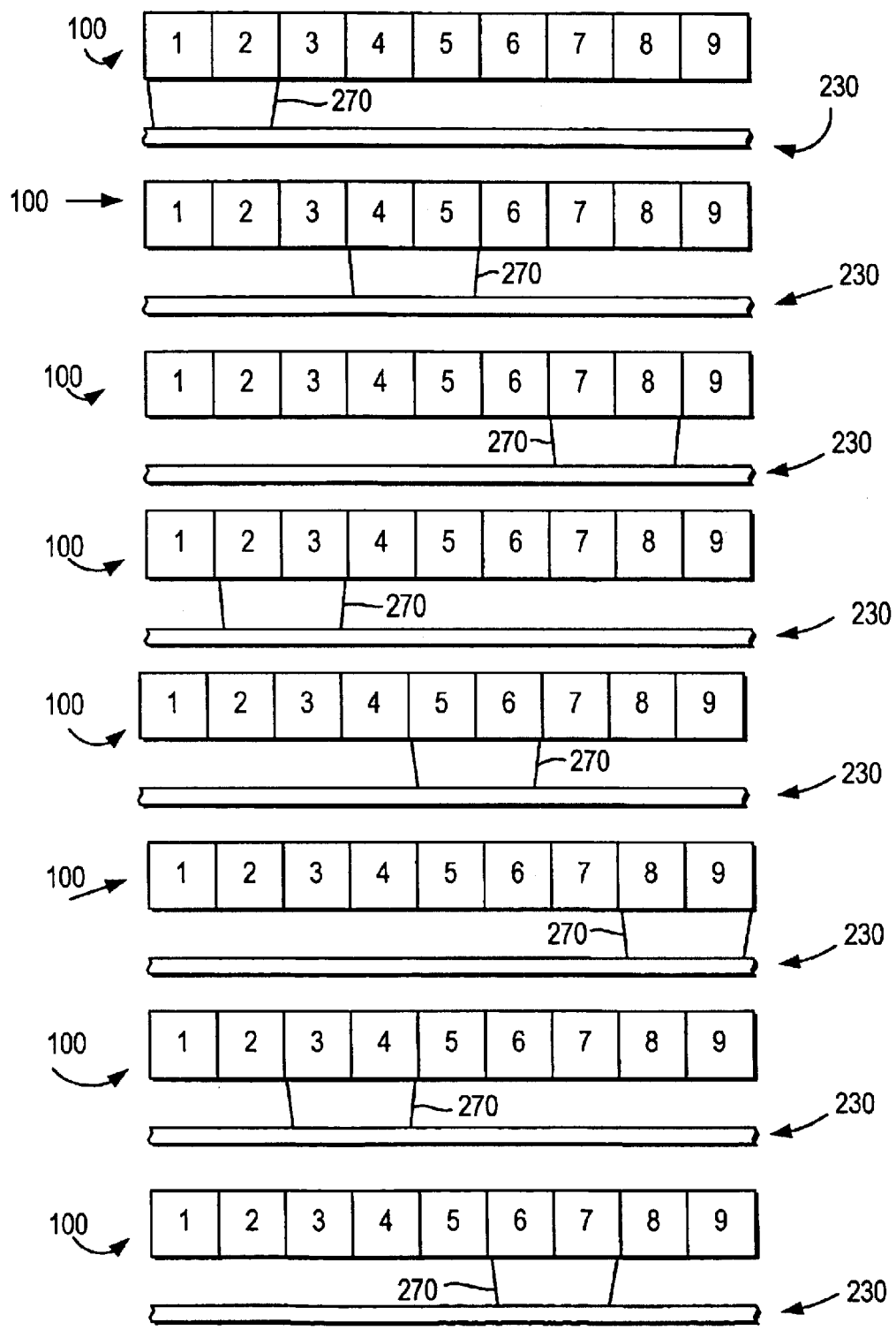
FIG. 12 is a collection of side views of an illustrative ultrasonic test sequence, in accordance with one embodiment of the present invention.

FIG. 12 illustrates a preferred firing sequence of transducer elements 110 of multi-element transducer 100, while combining two transducer elements 110 to produce a single transducer beam 270. FIG. 12 shows transducer elements 1 and 2 firing first, followed by transducer elements 4 and 5, followed by transducer elements 7 and 8, followed by transducer elements 2 and 3, followed by transducer elements 5 and 6, followed by transducer elements 8 and 9, followed by transducer elements 3 and 4, and finally followed by transducer elements 6 and 7.

When a transducer element of multi-element transducer 100 is excited, the multiple echoes generally occur only in that transducer element and possibly in the two transducer elements adjacent on either side of it. For example, when transducer element 2 is fired, echoes will occur in transducer element 2, and are likely to occur in transducer elements 1 and 3, but unlikely to occur in any other transducer elements. As a consequence, transducer elements 4 and 5 may be excited shortly after receiving sufficient reflections in transducer elements 1 and 2. Similarly, transducer elements 7 and 8 may be excited shortly after receiving sufficient reflections in transducer elements 4 and 5, and so on. In the arrangement illustrated in FIG. 12, transducers elements are excited in pairs, producing a beam with desirable length and sensitivity level, while minimizing cross-talk between transducer elements. Furthermore, each transducer element is excited twice, ensuring test overlapping and compensating for the gaps due to the decreased effective beam area. Processing may be done on a single channel by sequentially switching the output of each group of transducer elements to the next group and multiplexing the received signals on the single channel. This in turn increases the effective pulse repetition frequency (i.e, the rate at which a group of transducer elements emits an ultrasonic beam), thereby increasing the test throughput rate.

The order of firing need not be as shown in FIG. 12, as long as the groups of transducer elements that fire consecutively are separated by at least one transducer element. For example, transducer elements 2 and 3 may fire first, followed by transducer elements 7 and 8, followed by transducer elements 4 and 5, followed by transducer elements 1 and 2, followed by transducer elements 6 and 7, followed by transducer elements 3 and 4, followed by transducer elements 8 and 9, and finally followed by transducer elements 5 and 6. Moreover, the consecutively fired transducer elements need not be separated by at least a single transducer element. This is merely a measure to minimize transducer element cross-talk. For example, transducer elements 1 and 2 may fire first, followed by transducer elements 3 and 4, followed by transducer elements 5 and 6, followed by transducer elements 7 and 8, followed by transducer elements 2 and 3, followed by transducer elements 4 and 5, followed by transducer elements 6 and 7, and finally followed by transducer elements 8 and 9.

In yet another aspect of the present invention, different groups of transducer elements may be simultaneously fired. In a preferred embodiment of the present invention, two channels may be used. In this case, there may be four multiplexed firing periods. In the first period, transducer elements 1 and 2 may be connected to channel 1 and transducer elements 5 and 6 to channel 2. In the second period, transducer elements 4 and 5 may be connected to channel 1 and transducer elements 8 and 9 to channel 2. In the third period, transducer elements 7 and 8 may be connected to channel 1 and transducer elements 3 and 4 to channel 2. In the fourth period, transducer elements 2 and 3 may be connected to channel 1 and transducer elements 6 and 7 to channel 2. With two channels, an effective pulse repetition frequency of typically 2 kHz may be achieved by firing two pairs of transducer elements per period, in four consecutive periods.

In yet another preferred embodiment of the present invention, four channels may be used in order to achieve a more desirable effective pulse repetition frequency. In this case, there may be two firing periods. In the first period, transducer elements 1 and 2 may be connected to channel 1, transducer elements 3 and 4 to channel 2, transducer elements 5 and 6 to channel 3, and transducer elements 7 and 8 to channel 4. In the second period, transducer elements 2 and 3 may be connected to channel 1, transducer elements 4 and 5 to channel 2, transducer elements 6 and 7 to channel 3, and transducer elements 8 and 9 to channel 4. With four channels, an effective pulse repetition frequency of typically 4 kHz may be achieved by firing four pairs of transducer elements per period, in two consecutive periods. This arrangement can be applied, for example, to any linear array containing nine transducer elements. Choosing a multiplexing arrangement may depend on the size of the tube or bar being tested, the required water path and the types of defects being targeted.

FIG. 13 is a general schematic of a system 700 that employs a multi-element transducer for automated non-destructive testing. System 700 may be composed of tester 200, multi-element transducer 100, multiplexer 710, actuator 730, control circuitry 740, coupling capacitors 770, and analyzer 780. At least one multi-element transducer 100 may be mounted on tester 200, which may be a rotary tester as described above in connection with FIG. 6.

More than one multi-element transducer may be used and mounted on a rotary tester in order to detect different types of flaws. For instance, multiple multi-element transducers may be mounted on a rotary tester, each transducer containing nine transducer elements, with a separate channel dedicated to each multi-element transducer. These transducers may be oriented for clockwise, counter-clockwise, forward-, and reverse-looking shear wave testing and longitudinal wave testing. As a result, higher throughput rates can be obtained by using multi-element transducers through multiplexing techniques, while maintaining or even improving a tester's ability to detect flaws and take diameter or thickness measurements.

As shown in FIG. 13, cables 165 connect the different transducer elements of multi-element transducer 100 to multiplexer 710. Multiplexer 710 may multiplex signals from cables 165 into n available channels 720.

Each channel may be connected to actuator 730. Actuator 730 may be a pulser/receiver which sends electric signals to and receives electric signals from multi-element transducer 100 in order to drive the transducer elements and receive pulses respectively. Both multiplexer 710 and actuator 730 may be controlled by control circuitry 740. Control circuitry 740 may send control signals through connection 750 to multiplexer 710 in order to connect the appropriate channel(s) to the corresponding transducer element(s). Control circuitry 740 may further send control signals through connection 760 to instruct actuator 730 to send and receive appropriate electric signals through the appropriate channel to and from multi-element transducer 100 via multiplexer 710.

Tester 200 may be connected to analyzer 780, which may process and display emitted and received ultrasonic waveforms resulting from the testing. Analyzer 780 may dedicate an input to each one of channels 720. Analyzer 780 may run appropriate algorithms to detect flaws and take thickness or diameter measurements. Actuator 730 and analyzer 780 may be programmable for automated testing including flaw detection and thickness/diameter measurements. To facilitate the wiring that extends from tester 200, coupling capacitors 770, which are associated with each of n channels 720, may connect tester 770 to analyzer 780 and to any other external circuitry.

It is understood that multi-element transducer 100 as described in connection with the various figures is exemplary, and any other suitable multi-element transducer may be used (e.g., a linear array with a different number of transducer elements, a two-dimensional array, etc.).

The foregoing is merely illustrative of the principles of this invention and various modifications can be made by those skilled in the art without departing from the scope and spirit of the invention. For example, a multi-element transducer may be used in a testing apparatus other than a rotary tester. In a particular arrangement, the multi-element transducer may be used to test a flat object, such as a plate, without moving about its surface.

One skilled in the art will appreciate that the present invention can be practiced in other than the described embodiments, which are presented for purposes of illustration and not limitation, and the present invention is limited only by the claims which follow.

What is claimed is:

1. A method for non-destructive testing of an object using a multi-element transducer comprising a plurality of transducer elements, the method comprising:
    emitting a first ultrasonic pulse from a first group of two adjacent transducer elements;
    receiving first ultrasonic reflections from the first ultrasonic pulse with the first group of two adjacent transducers elements;
    emitting a second ultrasonic pulse from a second group of two adjacent transducer elements, wherein at least one of the transducer elements in the second group does not emit an ultrasonic pulse when the first group of transducer elements emits the first ultrasonic pulse;
    receiving second ultrasonic reflections from the second ultrasonic pulse with the second group of two adjacent transducer elements; and
    processing the first and second ultrasonic reflections to determine whether a flaw in the object exists.

2. The method of claim 1 further comprising scanning an outer surface of the object with the multi-element transducer, the scanning the outer surface of the object comprising:
    rotating the multi-element transducer about a longitudinal axis of the object, the object being cylindrically shaped, wherein the plurality of transducer elements remain facing the outer surface of the object;
    arranging the multi-element transducer so that it is perpendicular to a radial axis that intersects and is perpendicular to the longitudinal axis, the radial axis being rotatable about the longitudinal axis, the emitted ultrasonic pulses being substantially parallel to the radial axis; and
    moving the object in a direction along the longitudinal axis.

3. The method of claim 2 wherein the scanning the outer surface of the object further comprises arranging the multi-element transducer so that it intersects the radial axis in order to perform longitudinal wave inspection.

4. The method of claim 2 wherein the scanning the outer surface of the object further comprises arranging the multi-element transducer so that it is offset from the radial axis in order to perform shear wave inspection.

5. The method of claim 2 wherein the scanning the outer surface of the object further comprises scanning the outer surface of the object with a linear array of nine transducer elements consecutively numbered from one to nine, the method further comprising emitting ultrasonic pulses and receiving ultrasonic reflections with the following groups of transducer elements: transducer elements one and two, transducer elements two and three, transducer elements three and four, transducer elements four and five, transducer elements five and six, transducer elements six and seven, transducer elements seven and eight, and transducer elements eight and nine.

6. The method of claim 1 further comprising:
    connecting a channel to the first group of transducer elements for emitting the first ultrasonic pulse and for receiving the first ultrasonic reflections; and
    connecting the channel to the second group of transducer elements for emitting the second ultrasonic pulse and for receiving the second ultrasonic reflections.

7. The method of claim 6 wherein the channel is a first channel, the method further comprising:
    emitting a third ultrasonic pulse from a third group of two adjacent transducer elements, wherein none of the transducer elements in the third group is a transducer element in the first group; and
    connecting a second channel to the third group of transducer elements for emitting the third ultrasonic pulse when the first ultrasonic pulse is emitted.

8. An ultrasonic inspection system for non-destructive testing of an object, the ultrasonic inspection system comprising:
    a rotary testing unit having (a) a longitudinal axis about which the rotary testing unit rotates, (b) an outer wall, and (c) an inner wall, the rotary testing unit being configured to receive the object along the longitudinal axis;
    at least one multi-element transducer coupled to the inner wall of the rotary testing unit, wherein the at least one multi-element transducer comprises a plurality of transducer elements, wherein each one of the plurality of transducer elements is configured to emit an ultrasonic pulse and receive ultrasonic reflections from the object being tested;

an actuator configured to actuate the plurality of transducer elements in the at least one multi-element transducer.

9. The ultrasonic inspection system of claim 8 wherein the actuator is configured to (a) actuate the plurality of transducer elements individually or together in groups of adjacent transducer elements in order to emit ultrasonic pulses, and (b) receive ultrasonic reflections received by the actuated transducer elements from the object.

10. The ultrasonic inspection system of claim 9 further comprising a multiplexer coupled between the actuator and the at least one multi-element transducer, the actuator being configured to send and receive signals to the multiplexer through at least one channel, the multiplexer being configured to multiplex the signals sent to and received from the at least one multi-element transducer to the at least one channel.

11. The ultrasonic inspection system of claim 8 wherein the object is selected from the group consisting of a tube and a bar.

12. The ultrasonic inspection system of claim 8 further comprising an analyzer for processing the ultrasonic reflections received from the plurality of transducer elements.

13. The ultrasonic inspection system of claim 12 wherein the actuator is configured to automatically test the object by programmably actuating the plurality of transducer elements and passing the ultrasonic reflections received from the plurality of transducer elements to the analyzer for processing.

14. The ultrasonic inspection system of claim 8 wherein the plurality of transducer elements are arranged in a linear array such that the linear array remains parallel to the longitudinal axis.

15. The ultrasonic inspection system of claim 14 wherein the rotary testing unit has a radial axis that intersects and is perpendicular to the longitudinal axis, the radial axis being rotatable about the longitudinal axis together with the rotary testing unit, the linear array being arranged perpendicular to the radial axis, the ultrasonic emitted from the plurality of transducer elements being substantially parallel to the radial axis.

16. The ultrasonic inspection system of claim 15 wherein the radial axis intersects the linear array for performing longitudinal wave inspection of the object.

17. The ultrasonic inspection system of claim 16 wherein the linear array is offset from the radial axis for performing shear wave inspection of the object.

18. The ultrasonic inspection system of claim 8 wherein the at least one multi-element transducer comprises a linear array of nine transducer elements consecutively numbered from one to nine, the actuator being configured to actuate the plurality of transducer elements in the following groups of adjacent transducer elements: transducer elements one and two, transducer elements two and three, transducer elements three and four, transducer elements four and five, transducer elements five and six, transducer elements six and seven, transducer elements seven and eight, and transducer elements eight and nine.

* * * * *

UNITED STATES PATENT AND TRADEMARK OFFICE
CERTIFICATE OF CORRECTION

PATENT NO. : 6,725,721 B2
DATED : April 27, 2004
INVENTOR(S) : John Venczel

It is certified that error appears in the above-identified patent and that said Letters Patent is hereby corrected as shown below:

Title page,
Item [*] Notice, before "Apr. 27, 2004" delete "*".

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO.    : 6,725,721 B2
DATED         : April 27, 2004
INVENTOR(S)   : John Venczel It is certified that error appears in the above-identified patent and that said Letters Patent is hereby corrected as shown below:

<u>Title page,</u>
Item [45], Date of patent, "*Apr. 27, 2004" should read -- Apr. 27, 2004 --.
Item [*] Notice, delete "This patent is subject to a terminal disclaimer."

This certificate supersedes Certificate of Correction issued November 9, 2004.

Signed and Sealed this

First Day of February, 2005

JON W. DUDAS
*Director of the United States Patent and Trademark Office*